United States Patent [19]

Foster, Jr. et al.

[11] Patent Number: 5,023,460
[45] Date of Patent: Jun. 11, 1991

[54] TOOTHBRUSH SANITIZER

[75] Inventors: Robert W. Foster, Jr., Hinsdale; Jefferson L. Gentry, Deerfield, both of Ill.

[73] Assignee: Associated Mills Inc., Chicago, Ill.

[21] Appl. No.: 502,449

[22] Filed: Mar. 30, 1990

[51] Int. Cl.$^5$ ............................................. A61L 3/00
[52] U.S. Cl. .................... 250/455.1; 422/24
[58] Field of Search ............. 250/455.1, 454.1, 453.1, 250/504 R, 503.1; 422/24

[56] References Cited

U.S. PATENT DOCUMENTS

| | | | |
|---|---|---|---|
| 2,592,131 | 4/1952 | Farrar | 250/455.1 |
| 3,820,251 | 6/1974 | Abernathy | 250/455.1 |
| 3,955,922 | 5/1976 | Moulthrop | 422/24 |
| 4,625,119 | 11/1986 | Murdock, III | 250/455.1 |
| 4,740,706 | 4/1988 | Murdock, III | 250/455.1 |
| 4,803,364 | 2/1989 | Ritter | 250/455.1 |
| 4,806,770 | 2/1989 | Hylton et al. | 250/455.1 |
| 4,888,487 | 12/1989 | Ritter | 250/455.1 |
| 4,906,851 | 3/1990 | Beasley et al. | 250/455.1 |

OTHER PUBLICATIONS

A Clinical Study of Ultra-Violet Germicidal Light for Toothbrush Sanitization, 1988-1989, a study by the University of Oklahoma College of Dentistry.
"Replacing Toothbrush Can Fend Off Illness", by Tim Friend, U.S.A. Today.
Preliminary Report: Survival of Rhinovirus, a Virus Causing the Common Cold, on Toothbrushes, by Willard T. Charnetzky, Sally Paulson, Carolyn Applebaum.
National Semiconductor, LM555/LM555C Timer, pp. 9-33, 9-36 and 9-37.
Oral Bacteria, Numbers and Survival on Toothbrushes 1989, Dr. W. T. Charnetzky for Dentec Corporation.
Various advertisements for Dentec 4000 Toothbrush Sanitizer.
Various Comments regarding the Dentec 4000.
Bacteria Normally Transmitted in a Fecal-Oral Cycle, Numbers and Survival on Toothbrushes, 1989, by Dr. W. T. Charnetzky.

Primary Examiner—Jack I. Berman
Assistant Examiner—Kiet T. Nguyen
Attorney, Agent, or Firm—Laff, Whitesel, Conte & Saret

[57] ABSTRACT

A toothbrush sanitizer has a housing containing a centrally located elongated ultraviolet bulb surrounded by cavities for receiving standing toothbrushes. The cavities having one side open to receive ultraviolet light, have highly reflective surfaces to reflect light passing through said open side toward all sides of the toothbrushes, and have bottom contours which make the toothbrushes self-aligning. An electronic circuit lights the ultraviolet bulb with a short on, long off duty cycle. The initial on cycle is longer than the rest of the on cycles and occurs immediately after the cover is closed. A labyrinth seal permits passage of a cooling updraft of air while blocking an escape of ultraviolet light.

17 Claims, 2 Drawing Sheets

TOOTHBRUSH SANITIZER

This invention relates to devices for killing bacteria on personal appliances and more particularly to sanitizers for toothbrushes.

Some examples of prior toothbrush sanitizers are found in the following U.S. Pat. Nos.: 2,592,131; 3,820,251; 4,625,119; 4,740,706; 4,803,364; and 4,806,770.

Currently, much is being said and written about the dangers of contaminated tooth brushes. One recommendation is that toothbrushes be replaced every two or three months. Another recommendation is that a toothbrush should be replaced every two weeks even if the user is in good health. Daily replacement is recommended if the user is sick or recovering from major surgery or otherwise especially susceptible to infection.

This interest in toothbrush contamination had led some people to suggest that toothbrushes should be disposable. However, a disposable brush usually has such low cost bristles that, even when new, they provide less than a satisfactory cleaning. Another suggestion is that brushes be sterilized after each use so that a high quality brush with a fine cleaning ability can be affordable and still not become a breeding ground for bacteria.

Most toothbrush sterilizers use ultraviolet light to kill bacteria. Since ultraviolet light is dangerous to the user's health, such a sterilizer must have many safety features to prevent an accidental exposure of the light. Also, since ultraviolet light severely degrades plastic, the bristles should be protected from over radiation.

Another recommendation is that toothbrushes be stored in a cool dry room since hot, humid bathrooms are ideal environments for a bacteria culture. This means that the drippings from the toothbrush should be contained to preclude unsightly accumulations in, say, a bedroom. However, the nature of the drippings is such that cleaning may be difficult. Therefore, it would be good to provide a collection device which could be placed in a dishwasher.

Yet another consideration which has been overlooked by the designers of most toothbrush sanitizers is the handle of the toothbrush. The sanitizers are usually designed to clean the bristles, with no provision for sterilization of the handle, itself. However, an end portion of the handle also enters the oral cavity. If the handle is exposed to ultraviolet light in prior sanitizers, then a very limited length of only one side is exposed to the sanitizing effect. The handle is, thus, left with unsanitized areas.

For these and other reasons, there have not heretofore been any truly satisfactory low cost means for or methods of sterilizing substantially entire toothbrushes, in the home environment.

Accordingly, an object of this invention is to provide new and novel means for and methods of sterilizing substantially entire toothbrushes. Here, an object is to provide an extremely low cost electrical control circuit which gives excellent results so that the sterilizer is affordable to all. In particular, an object is to provide suitable sanitizing with a cyclically recurring duty cycle, such as an initial three to four minutes sterilizing cycle followed by an approximate thirty minute off cycle and, thereafter, cyclically providing approximately a two to three minute on, thirty minute off sequence of sterilizing, for example. Yet another object is to provide a duty cycle which immediately gives an on cycle to dry the brush as soon as it is placed in the sterilizer, as distinguished from the prior art where a relatively long immediate off cycle (while the brush remains wet) is followed by an on sterilizing cycle.

Still another object is to provide sterilization surrounding 360° of the toothbrush handle.

Yet another object is to provide an easily cleaned device for collecting toothbrush drippings.

In keeping with an aspect of the invention, these and other objects are accomplished by a plastic housing having a source of ultraviolet light surrounded by a series of vertically oriented cavities for receiving toothbrushes. The cavities are arcuate in cross-section and may be plated with a mirror-like surface to reflect ultraviolet light on all sides of the toothbrushes. In some models, the plastic used to make the housing is a highly reflective plastic with a highly reflective surface so that a plated surface may not always be required. The arcuate surface may have any of many suitable shapes; however, it preferably focuses the light on the back of the toothbrush handle. For example, the arcuate surface might be a parabolic shape. An electronic circuit provides a duty cycle for periodically supplying the ultraviolet light, with an initially on cycle. Preferably, the plastic housing sets on a removable coaster which collects the toothbrush drippings. A number of safety features prevents the ultraviolet light from escaping from the housing.

A prepared embodiment of the invention is seen in the attached drawings wherein.

Figure 1:
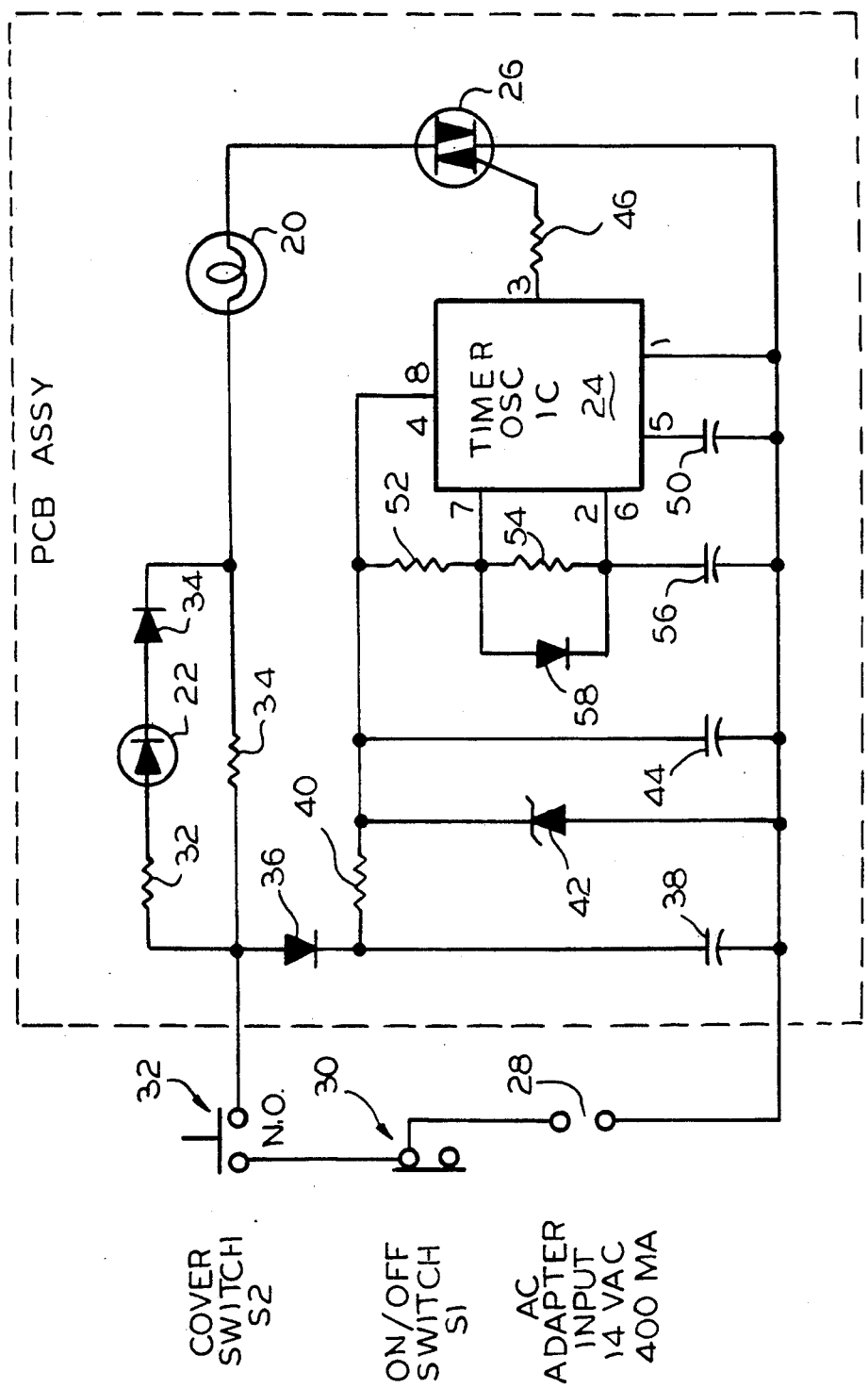
FIG. 1 is a schematic circuit diagram showing a control circuit for illuminating the ultraviolet lamp.

FIG. 1 shows an astable, self-triggering control circuit for the ultraviolet lamp, as including an ultraviolet lamp 20, an LED 22, a timer 24, and a triac 26. The timer 24 is a type LM555 which is commercially available from many sources, one of which is Motorola. The power is applied across terminals 28. This power is preferably supplied from a standard commercial A.C. adapter which plugs into a wall outlet and provides 14 VAC, with limited current (400 MA) so that there is no potentially hazardous shock condition.

An off/on switch is provided at 30 for selectively turning the sterilizer off and on. Another and cover actuated switch 32 prevents the lamp from lighting when the cover is off, thereby preventing the user from being accidently exposed to ultraviolet light.

Coupled to the switches is an LED 22 which lights anytime that the ultraviolet lamp 20 is lit. First, this informs the user when ultraviolet light is present. Second, it indicates when the lamp is burned out. Heretofore, either the user had to lift off the cap or a window had to be provided in the housing so that the lit or unlit condition of the bulb could be seen. Either way, the user might be exposed to ultraviolet light. A current limiting resistor 32 and rectifying diode 34 are provided in series with the LED. A resistor 34 is coupled across the series circuit to provide a voltage drop which is sufficient to light the lamp. A triac 26 completes a circuit to cyclically light the lamp-LED combination.

A diode 36 provides rectified voltage to supply DC to the electronic components in the circuit. Capacitor 38 provides smoothing for the rectified DC. A resistor 40 provides a proper bias potential for a zener diode 42 which regulates the level of the DC potential. Capacitor 44 provides a bypass for radio frequency noise. The timer 24 has a "3" pin coupled through a resistor 46 to the gate of the triac 26 to turn it off/on, and therefore to turn the ultraviolet lamp 20 off/on. The timing is such that, after the cover is replaced, the light switches on immediately.

Capacitor 50 is a termination required by the design of the timer/oscillator 24.

Resistors 52, 54 and capacitor 56 provide an RC timing circuit for cyclically switching the lamp off/on. If only the resistors are provided, there would tend to be a uniform on/off cycle. However, a diode 58 is coupled to short circuit the resistor 54 for DC current in one direction. Thus, in the charge/discharge cycle of capacitor 56, there is a non-uniformity wherein the timer/oscillator 24 responds for two minutes when the polarity of the DC makes diode 58 conductive to shunt resistor 54 and responds for thirty minutes when the DC polarity switches off the diode and current must pass through resistor 54. In one embodiment, resistor 52 is 680k ohms and resistor 54 is 10 megohms.

Figure 3:
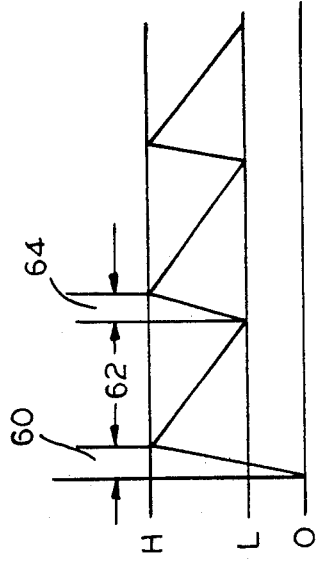
FIG. 3 is a vertical cross-section of the sterilizer.

FIG. 3 graphically illustrates the duty cycle of the timer/oscillator 24. When the cover of the appliance is opened, the cover switch 32 opens the circuit and deenergizes it. The capacitor 56 is completely discharged, at the ground or "0" potential. When the cover is replaced to close switch 32, the capacitor 56 charges to a high voltage level H over a three or four minute period of time 60. At the high voltage H, the timer/oscillator 24 applies a voltage with reverse polarity which switches off the diode 58 and thus, forces current through resistor 54. It takes thirty or so minutes 62 for the capacitor to discharge through resistors 52, 54 to a low level L where the timer again reverses polarity to switch on the diode and bypass the resistor 54. The capacitor only requires two or three minutes 64 to charge from the low level L to the high level when resistor 54 is effectively excluded from the circuit. Thereafter, and until the cover is again removed, the duty cycle is two or three minutes on and thirty or so minutes off. Of course, the durations of the on/off cycles may be charged, as may be desired.

During the two and three (for example) minute intervals 60, 64, the timer/oscillator 24 applies a potential via resistor 46 to switch on the triac 26 and, therefore, to light ultraviolet lamp 20 and LED 22. During the thirty (for example) minute intervals, timer/oscillator 24 applies a potential to switch off the triac 26, lamp 20, and LED 22.

Figure 4:
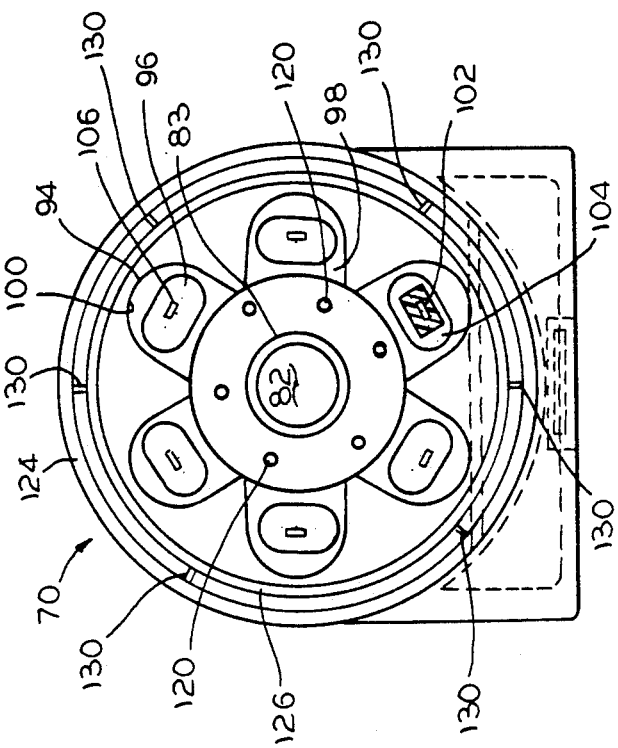
FIG. 4 is a plan view of the sterilizer taken along line 4—4 of FIG. 3.

FIGS. 3, 4 show two cross-sections of a toothbrush sanitizer 70 which is controlled by the circuit of FIG. 1. The housing comprises a cover 72, a base 74, and a tray 76. The cover 72 is a simple cup. The tray 76 may be removed and placed in a dishwasher for cleaning.e A central platform 78 supports a socket base 80 for receiving an elongated cylindrical ultraviolet bulb 82, for example. A clear and transparent to ultraviolet light ring (6 mm high in one embodiment) 83 attaches to the central platform 78 to support the toothbrushes which may lean toward but not touch the bulb, thereby protecting both the brushes and bulb. Dependent from the central platform base 78 and supported at the bottom by members 79, 79 is a printed circuit card 84. A jack socket 28 provides a connector for the power supply to connect into. An off/on switch is shown at 30. The LED is seen at 22.

Figure 2:
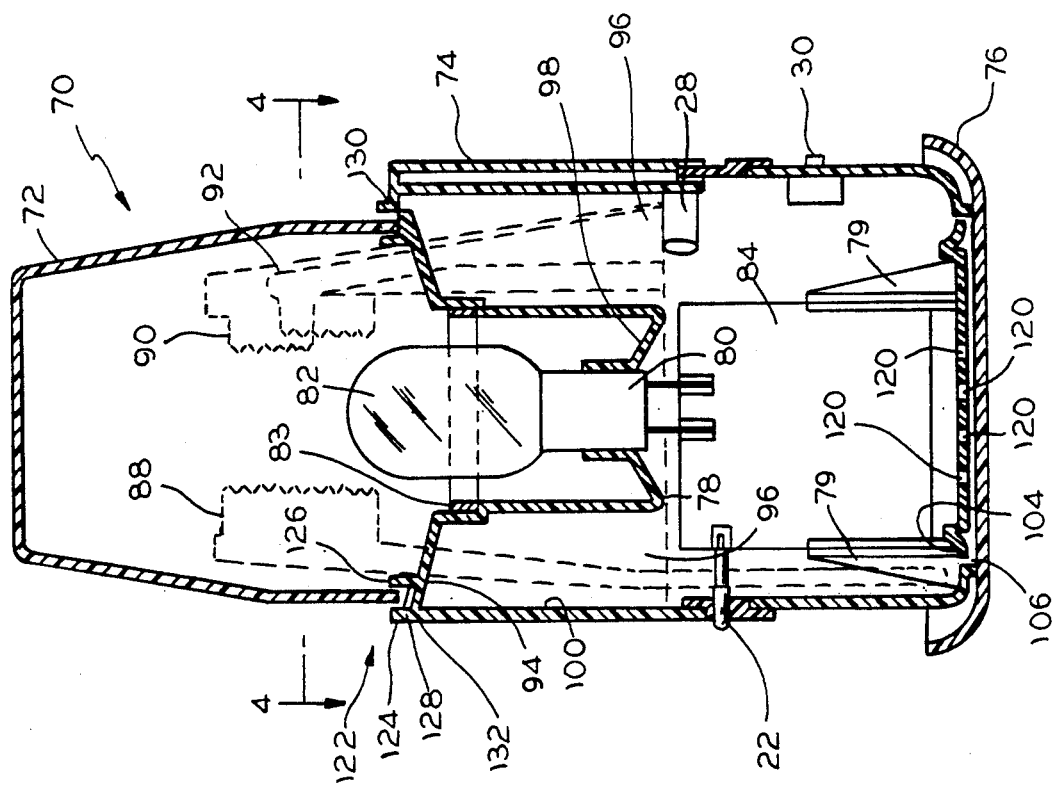
FIG. 2 is a graph for explaining how an initial illumination of the lamp may continue for a longer than usual on period of time.

A number of different types of toothbrushes are shown FIG. 2 by dashed lines, such as a standard toothbrush 88 and two different types 90, 92 of electric toothbrushes. There are openings 94, 96 through which the handle of the standard toothbrush 88 passes. A step 98 on the central platform stops and supports the bottoms of the electric toothbrushes. The opening 96 provides drainage for the electric toothbrush drippings.

FIG. 4 shows the plan view of the housing. The opening 94 at the top of the housing is arcuate so that, when given a highly reflective or mirror surface 100, it reflects ultraviolet light onto all sides of the toothbrush handle. The reflective surface may result from the reflectivity of the plastic used to make the housing or from an electro-plating placed over the plastic. While the arcuate shape may be any suitable shape, it is preferably designed to focus the reflected light onto all non-directly lit sides of the brush. For example, the cross-sectional shapes may be parabolic.

The dish or cup shaped member 104 (FIG. 4) has an elongated shape which orients the handle 102 of a toothbrush so that its bristles point directly toward the bulb. The cup shape 104 is large enough to catch drippings from the electric toothbrushes 90, 92. A drainage hole 106 is formed in the bottom of each of the cups 104 to drain into the tray 76 under the housing.

With this background, and from an inspection of FIGS. 3, 4, it is apparent that the ultraviolet light of lamp 82 reaches all sides of substantially the entire brush, bristles, and handles so that everything which goes into the mouth (not just the bristles) is sanitized.

If the housing is left unventilated, it becomes a warm moist environment which provides an environment for growing a bacteria culture in areas which may not be adequately radiated by the ultraviolet light. Therefore, to prevent this unwanted side effect, the interior of the housing is cooled by an updraft of air.

More particularly, cool air enters the bottom of the housing via the drainage holes 106, and cooling holes 120. The cool air passes upwardly over the printed circuit card 84, preventing it from being over heated. The cooling updraft of air continues and passes the bulb 86, which is the heat source, and escapes via a labyrinth seal 122. The seal is formed by two concentric upstanding walls 124, 126 which provide between them a space that is wider than the thickness of the cup wall 128. At spaced intervals around the circumference of the cup three to six small projections 130 prevent the cup from settling to the bottom of the area in which it sets, thus leaving a labyrinth path through which air, but not light, may pass. To further restrict the passage of light, at least part of the labyrinth is made non-reflective, for example, the bottom of the space between walls 124, 126 may be colored black. One way of doing this is to place a black washer 132 in the bottom of the space and, perhaps, to bond it in place.

Those who are skilled in the art will readily perceive how to modify the invention. Therefore, the appended claims are to be construed to cover all equivalent structures which fall within the true scope and spirit of the invention.

The claimed invention is:

1. A toothbrush sanitizer comprising an irradiating source of ultraviolet light; a housing having a plurality of areas for supporting toothbrushes in positions which expose substantially all of the parts of said toothbrushes which enter the mouth, including their bristles and handles, to an irradiation of light from said source; said housing having internal contours which direct the light to completely surround said brush so that all sides of both said bristles and handles of said brush are irradiated by said light, said housing being closed by a cover to contain all ultraviolet light from said source, cover switch means for preventing said light from lighting except when said cover is in place to contain said light, said cover having a lip with a predetermined wall thickness, and a labyrinth seal at the lip of said cover, said seal comprising two upstanding concentric walls on said housing separated by a space which is wider than said predetermined wall thickness of said cover lip, means for holding said cover in an elevated position between said concentric walls, and openings in the bottom of said housing to provide an entrance for air in order to provide an updraft of cool air between said openings and said labyrinth seal.

2. The sanitizer of claim 1 and means for making at least part of said labyrinth seal a non-light reflecting surface.

3. The sanitizer of claim 1 and means for periodically causing said source to irradiate said ultraviolet light with a duty cycle of cyclically recurring short periods of light "on" time and long periods of light "off" time.

4. The sanitizer of claim 3 wherein a first of said short periods of light "on" time is longer after said cover is first closed over said housing than it is later during said cyclically recurring periods.

5. The sanitizer of claim 4 and control means for causing said cyclically recurring periods of said irradiation, said control means including a timer having a resistor-capacitor circuit for setting a duty cycle and a diode coupled across a part of a resistor forming said resistor-capacitor circuit whereby the circuit times a longer cycle period when a polarity of voltage in said circuit is in one direction and a shorter cycle period when said polarity is reversed.

6. The sanitizer of claim 5 further comprising circuit means for causing said resistor-capacitor circuit to charge from zero volts when said cover switch is first closed and thereafter to charge from a low voltage level, thus changing the timing of the duty cycle after said original charge of said RC circuit.

7. A toothbrush sanitizer comprising an irradiating source of ultraviolet light; a housing having a plurality of areas for supporting toothbrushes in positions which expose substantially all of the parts of said toothbrushes which enter the mouth, including their bristles and handles, to an irradiation of light from said source; said housing having internal contours which direct the light to completely surround said brush so that all sides of both said bristles and handles of said brush are irradiated by said light, control means for causing said irradiation including a timer having a resistor-capacitor circuit for setting a duty cycle and a diode coupled across a part of a resistor forming said resistor-capacitor circuit whereby the circuit times a longer cycle period when a polarity of voltage in said circuit is in one direction and a shorter cycle period when said polarity is reversed.

8. The sanitizer of claim 7 further comprising circuit means for causing said resistor-capacitor circuit to charge from zero volts when said cover switch is first closed and thereafter to charge from a low voltage level, thus changing the timing of the duty cycle after said original charge of said RC circuit.

9. A toothbrush sanitizer comprising an irradiating source of ultraviolet light; an housing having a plurality of areas for supporting toothbrushes in positions which expose substantially all of the parts of said toothbrushes which enter the mouth, including their bristles and handles, to an irradiation of light from said source; said housing having internal contours which direct the light to completely surround said brush so that all sides of both said bristles and handles of said brush are irradiated by said light, each of said areas for supporting toothbrushes having an arcuate contour with a reflective surface, said toothbrush handle being centrally located within said arcuate contours so that light is reflected from said surface and onto said handle when said source is irradiating light.

10. A sanitizer for elongated personal appliances objects, said sanitizer having a centrally located elongated source of ultraviolet light, a plurality of cavities each having an elongated open dimension facing and aligned with the elongation of said source of light whereby light may enter said cavities along the length of said elongated open dimension, a closed side of each of said cavities being shaped to direct light from said source onto an object standing in said cavity, said closed sides of said cavities having a highly light reflective surface, and means beneath said cavities for collecting drippings from said cavities.

11. The sanitizer of claim 10 wherein said means for collecting drippings is removable for easy clean-up.

12. The sanitizer of claim 10 wherein said highly reflective surface is plated with a mirror-like material.

13. The sanitizer of claim 10 and a cover with switch means for preventing light from said source from escaping said housing.

14. A sanitizer for elongated personal appliances objects, said sanitizer having a centrally located elongated source of ultraviolet light, a plurality of cavities each having an elongated open dimension facing and aligned with the elongation of said source of light whereby light may enter said cavities along the length of said elongated open dimension, a closed side of each of said cavities being shaped to direct light from said source onto an object standing in said cavity said closed sides of said cavities having a highly light reflective surface, means beneath said cavities for collecting drippings from said cavities, switch means for preventing light from said source from escaping said housing when said cover is removed, pilot light means associated with the exterior of said housing for indicating when said light source is active within said housing, and circuit means for lighting said light source with a duty cycle which is a short time on and a long time off, beginning with a longer than average on time after the cover is first replaced on said housing.

15. The sanitizer of claim 14 and a labyrinth seal at a perimeter of said cover for passing heat while preventing a passage of light.

16. The sanitizer of claim 14 and means comprising a ring which is transparent to ultraviolet light interposed between said source of ultraviolet light and toothbrushes in said cavities in order to keep said toothbrushes from touching said source of ultraviolet light without blocking a transmission of said light.

17. A sanitizer for elongated personal appliances objects, said sanitizer having a centrally located elongated source of ultraviolet light, a plurality of cavities each having an elongated open dimension facing and aligned with the elongation of said source of light whereby light may enter said cavities along the length of said elongated open dimension, a closed side of each of said cavities being shaped to direct light from said source onto an object standing in said cavity, said closed sides of said cavities having a highly light reflective surface, means beneath said cavities for collecting drippings from said cavities, and means comprising a ring which is transparent to ultraviolet light interposed between said source of ultraviolet light and said object in order to keep said object from touching said bulb without blocking said light.

* * * * *